United States Patent
Gulati et al.

(10) Patent No.: US 9,731,060 B2
(45) Date of Patent: Aug. 15, 2017

(54) AUTOMATED PRE-FILTRATION AIR MANAGEMENT AND FILTRATION SYSTEMS AND METHODS

(71) Applicant: Fenwal, Inc., Lake Zurich, IL (US)

(72) Inventors: Kartike Gulati, Naperville, IL (US); Grant S. Benjamin, Ingleside, IL (US)

(73) Assignee: Fenwal, Inc., Lake Zurich, IL (US)

( * ) Notice: Subject to any disclaimer, the term of this patent is extended or adjusted under 35 U.S.C. 154(b) by 226 days.

(21) Appl. No.: 14/328,485

(22) Filed: Jul. 10, 2014

(65) Prior Publication Data

US 2014/0319074 A1   Oct. 30, 2014

Related U.S. Application Data

(62) Division of application No. 12/392,695, filed on Feb. 25, 2009, now abandoned.

(60) Provisional application No. 61/031,933, filed on Feb. 27, 2008.

(51) Int. Cl.
*A61M 1/02* (2006.01)
*A61M 1/10* (2006.01)
*A61M 1/36* (2006.01)

(52) U.S. Cl.
CPC ........ *A61M 1/3644* (2014.02); *A61M 1/0222* (2014.02); *A61M 1/0231* (2014.02); *A61M 1/3626* (2013.01); *A61M 1/3643* (2013.01); *A61M 1/10* (2013.01); *A61M 1/3639* (2013.01)

(58) Field of Classification Search
None
See application file for complete search history.

(56) References Cited

U.S. PATENT DOCUMENTS 5,954,971 A * 9/1999 Pages .................. A61M 1/3639
                                              210/103
6,171,493 B1 * 1/2001 Zia ...................... A61M 1/0209
                                              210/188

* cited by examiner

*Primary Examiner* — Krishnan S Menon
(74) *Attorney, Agent, or Firm* — Cook Alex Ltd.

(57) ABSTRACT

Filtration systems and methods using a pump and pressure sensor are provided for improved efficiency in fluid filtration systems. A filtration system includes a pre-filter container joined to a post-filter container by a filter line having a filter. To reduce the time required for filtration a pump and pressure sensor are included in a filter inlet flow path. The pump also is used to provide air management in the system via pre-filtration evacuation of air from at least the filter.

17 Claims, 3 Drawing Sheets

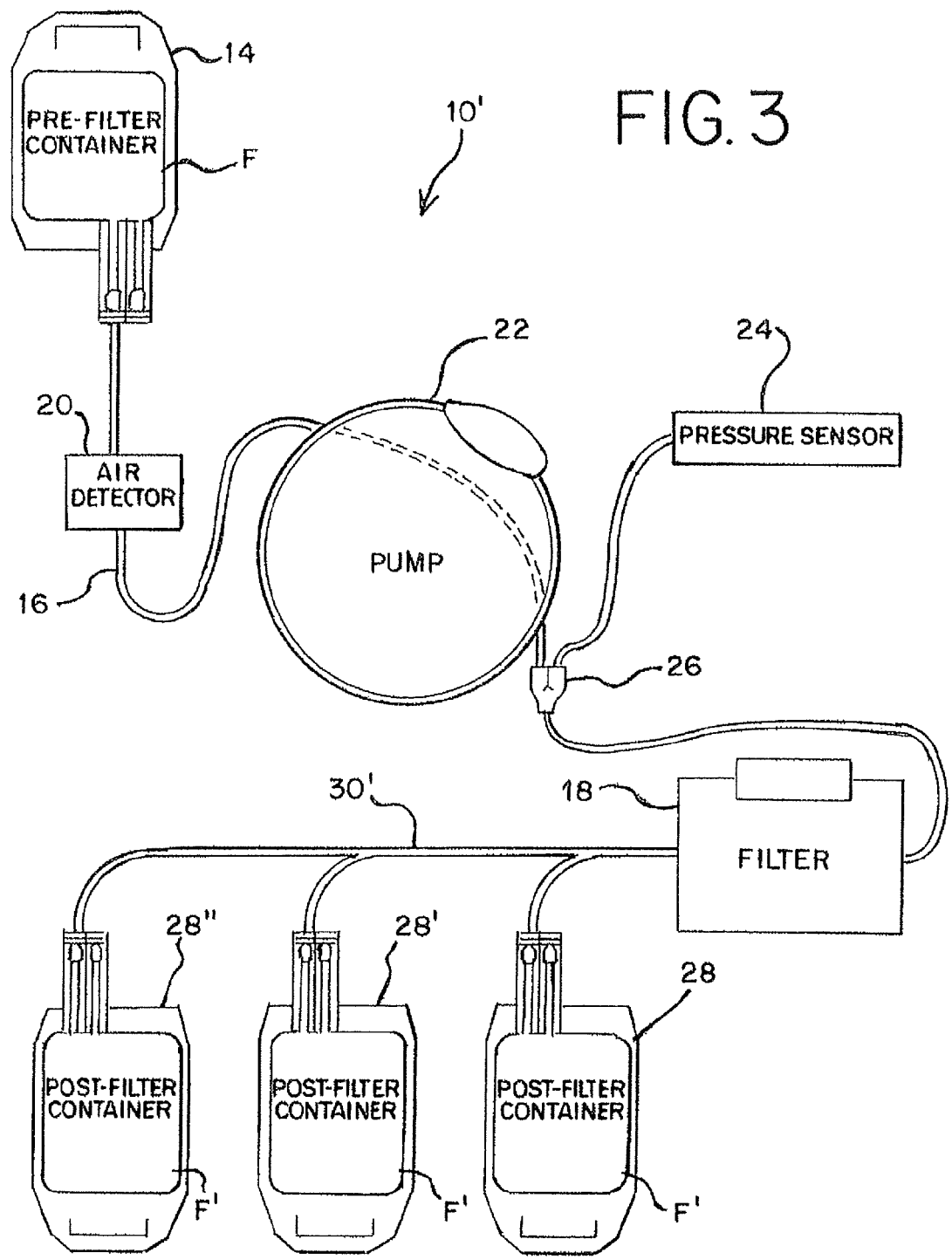

AUTOMATED PRE-FILTRATION AIR MANAGEMENT AND FILTRATION SYSTEMS AND METHODS

CROSS-REFERENCE TO RELATED APPLICATIONS

This is a divisional application of prior U.S. application Ser. No. 12/392,695, filed Feb. 25, 2009, which claims the benefit of U.S. Provisional Patent Application No. 61/031,933, filed on Feb. 27, 2008, the disclosure of which is hereby incorporated herein by reference.

BACKGROUND

Field of the Disclosure

This disclosure generally relates to apparatus and methods for filtering a fluid, such as but not limited to a biological fluid. More particularly, this disclosure relates to apparatus and methods for filtering a biological fluid, such as blood that includes the removal of leukocytes from whole blood or a blood component. The disclosure further relates to systems and methods that allow for automated air management, filtration and recovery of blood or blood components.

Description of Related Art

Prior to transfusion of blood or a blood component into a recipient, it is common to filter the blood product to remove leukocytes. This process is commonly referred to as leukoreduction. It may be desirable to remove leukocytes from blood or a blood component prior to transfusion because they can trigger a broad range of graft-versus-host adverse reactions in a recipient, ranging from minor effects, such as chills, to more serious effects, such as the transmission of cytomegalovirus, which can be fatal to recipients with weakened immune systems.

Commonly, blood processing with leukoreduction involves the transfer of blood or a blood component from a pre-filter fluid container to a post-filter fluid container through a tubing line having a leukoreduction filter. The filter and tubing line typically include a quantity of air or gas (non-liquid and non-solid), generally referred to hereafter as "air", that is pushed out of the tubing and filter upon priming the same during a filtration application. It is desired to prevent this air from moving into the post-filter container and remaining there, because such air aggregation can prevent complete filtration of the blood, as will be described in greater detail herein, and decrease the quality and storability of the filtered blood. Even when the blood or blood component is used a short time after filtration, there is a general preference among users to have as little air in the post-filter container as possible.

Known approaches to air management include filtration systems that are vented to the atmosphere or an air container and those incorporating a bypass line. For example, U.S. Pat. No. 5,863,436 to Matkovich, which is hereby incorporated herein by reference, describes several leukoreduction systems incorporating one or more air vents. One commercial system according to the description of Matkovich is the Pall SAVE™ system, which is incorporated into the Leukotrap® WB Filtration System from Pall Corporation of Glen Cove, N.Y. The Leukotrap® WB Filtration System comprises a pre-filter container connected to a post-filter container by a filter line having a leukoreduction filter. A pre-filter air vent is associated with the filter line between the pre-filter container and the filter, while a post-filter air vent is associated with the filter line between the filter and the post-filter container. In use, the pre-filter container is hung above the post-filter container and a cannula of the pre-filter container is broken to allow fluid flow into the filter line. The fluid is prevented from flowing into the pre-filter air vent by a removable cap, so it instead flows into the filter. The filter is allowed to prime, with air exiting the system through the post-filter air vent. When the filter is fully primed, a cannula between the post-filter vent and the post-filter container is broken to allow fluid and air to flow into the post-filter container. Due to pressure differentials in the system, the filtration process ceases prior to complete filtration of all the fluid, i.e., with an amount of fluid remaining in the filter. At that time, the cap on the pre-filter air vent is removed to allow air to enter the filter line and purge any remaining fluid from the inlet side of the filter.

One problem with systems according to the foregoing description is that no means are provided to remove air from the post-filter container, either during or after filtration. While the post-filter vent removes the air that is purged from the filter, air may be initially present in the system at other locations, such as in the containers or the tubing, as a result of the manufacturing process. This air is pushed into the post-filter container during filtration and can lead to the aforementioned diminished performance and quality concerns if not removed during or after filtration.

In response to the foregoing problem, leukoreduction systems incorporating bypass lines allow removal of air from the post-filter container during and/or after filtration. Several examples of known leukoreduction systems with bypass lines are described in U.S. Pat. No. 6,358,420 to Blickhan et al., which is hereby incorporated herein by reference. In one system, a pre-filter container is connected to a post-filter container by a filter line having a leukoreduction filter. Tubing providing a bypass line is connected to the filter line at opposite sides of the filter, thereby allowing for fluid communication between the containers along a path that bypasses the filter. The bypass line is provided with a one-way valve, typically a check valve, which only allows air and fluid flow toward the pre-filter container from the post-filter container. In use, the pre-filter container is hung above the post-filter container and a cannula of the pre-filter container is broken to allow fluid flow into the filter line. The fluid is prevented from flowing through the bypass line and into the post-filter container by the one-way valve. The fluid flows through the filter and into the post-filter container, along with an amount of air. Due to pressure differentials in the system, the filtration process ceases prior to complete filtration of the fluid, i.e., with an amount of fluid remaining in the filter. At that time, a slide clamp is placed on the filter line, between the filter and the post-filter container, and the post-filter container is squeezed to force air through the bypass line and toward the pre-filter container. Squeezing the post-filter container to remove air is sometimes referred to as "burping" the container. When the post-filter container has been "burped," the clamp is removed from the filter line and the filter is allowed to more completely drain.

According to another leukoreduction system described in Blickhan et al., one end of the bypass line is connected to the filter line at a position between the pre-filter container and the filter, while the other end is connected directly to the post-filter container. This system operates similarly to the previously described system of Blickhan et al. to filter blood or a blood component and remove air from the post-filter container.

While systems incorporating bypass lines represent improvements over the systems of Matkovich in terms of air removal from the post-filter container, the need to manually "burp" the container to remove air may be problematic. In particular, the amount of air removal is directly dependent on the strength and skill of the user, which can potentially lead to insufficient or incomplete air removal. In addition, the effort required by the operator in terms of having to bend down or kneel to reach the post-filter container and then having to apply a squeezing force with both hands is undesirable, and can lead to operator fatigue, error and lower quality results.

A more recent approach to eliminating the manual "burping" step is to allow for automatic "burping" of the post-filter container. Several such systems are described in U.S. Pat. No. 6,171,493 to Zia et al., which is hereby incorporated herein by reference. Rather than connecting the bypass line to one or more sections of the filter line, one end of the bypass line is directly connected to the pre-filter container and the other end of the bypass line is directly connected to the post-filter container. The pre-filter container is hung above the post-filter container and, in one embodiment, a loop portion of the filter line is elevated above the fluid level in the pre-filter container to prevent fluid from flowing through the bypass line and into the post-filter container. A clamp on the filter line is opened to allow fluid flow through the filter line and the filter. Air in the filter is pushed into the post-filter container by the blood and begins to accumulate therein and/or to leak from the post-filter container into the bypass line. When the pressure in the post-filter container reaches a sufficient level and the pressure in the pre-filter container decreases sufficiently (typically to a vacuum state), some of the air moves up the bypass line, through the loop portion, and into the pre-filter container. The return of air to the pre-filter container increases the pressure above the filter and assists in more completely draining any remaining fluid from the filter.

In theory, the "burping" system of Zia et al. improves on previously known systems by automatically removing air from the post-filter container, without requiring a manual "burping" operation. However, the efficiency of the Zia et al. system is contingent on the pressure differential between the post-filter container and the pre-filter container. Optimal filtration results are achieved when pressure in the post-filter container is maximized. If only a small amount of fluid is to be filtered, then the post-filter container will remain relatively empty and the pressure developed therein will not be sufficient to re-circulate the air to the pre-filter container. In such situations, the post-filter container must be manually squeezed to remove air, thereby representing a failure of the intended automatic "burping" feature.

There are systems which use a different method referred to as retro-priming. In transfusion medicine, this concept is used in red blood cell filtration where before filtration by gravity starts, the post-filter container contains a solution such as Ad-Sol and the pre-filter container contains packed red blood cells. This method may be used by gravity, such as by initially suspending the post-filter container at a height above the other components, or manually such as by squeezing the post-filter container to force the fluid up through the post-filter container, post-filter flow path, and filter until the air in these portions of the system is forced upward toward and/or into the pre-filter container that contains the fluid to be filtered. Depending on the volume of each component in the system, the retro-priming may be continued to additionally force the air to continue to flow upward through the pre-filter flow path and to all be deposited into the pre-filter container, along with some of the solution from the post-filter container. This method has proven successful in evacuating air from a system, but includes the drawback of extra time required, as well as requiring intervention and manual effort by an operator to affect the changes in height or squeezing of the components.

Even more recent air management systems and methods are described in U.S. patent application Ser. No. 11/618,286, which is hereby incorporated herein by reference. The systems in this application incorporate gravity-based filtration, but include apparatus that is adapted to limit an amount of air in the post-filter container during and after filtration of a biological fluid by reducing the maximum volume of the post-filter container, and by using a bypass line to assist in air removal. A post-filter container normally would be expandable to a maximum volume that may be equal to or exceed the volume of the pre-filter container. However, by use of a smaller post-filter container or use of a restrictor or volume restriction device, such as for example a band around the post-filter container, or locating the post-filter container between a pair of plates, the maximum capacity of the post-filter container can be reduced. The restriction on the growth of the post-filter container tends to increase the effectiveness of the transmission of air through the bypass line and ultimately improves the recovery of fluid through the filter, as disclosed in the application.

Another separate problem with the foregoing systems is that they merely utilize gravity to move the fluid during the filtration process. The rate of gravity filtration can vary widely and is dependent on the density of the fluid being filtered, the temperature, the inner diameter of the tubing used in the system, the relative heights of the pre-filter container, post-filter container and any of the intermediate components, such as the filter. The force of gravity is a constant, nevertheless, gravity filtrations can range in time from tens of minutes to a few hours. Thus, not only is the amount of time objectionable, but the unpredictability of the time required to complete the process is bothersome and inconvenient to operators and for scheduling purposes.

While some of the systems described above have worked satisfactorily, there remains a need for apparatus and methods for more efficiently filtering fluid products with respect to the amount and predictability of the time required to complete the process, as well as with respect to the removal of air from a post-filter container, and with less dependence on the amount of fluid to be filtered.

SUMMARY

The present disclosure sets forth several aspects of the devices, systems and methods described below.

In one aspect, a filtration system is provided with a pre-filter container adapted to contain a fluid, a filter, and a post-filter container adapted to contain a filtered fluid. A filter inlet flow path extends between the pre-filter container and the filter and a filter outlet flow path extends between the filter and the post-filter container. A pump is located in the filter inlet flow path and the pump provides pre-filtration evacuation of air from at least the filter.

In another aspect, a method of filtering a fluid includes providing a pre-filter container, providing a post-filter container, providing a filter line having a filter between the pre-filter container and the post-filter container, and providing a pump and a pressure sensor in communication with the pre-filter container and the filter. The method further includes flowing air from at least the filter into the pre-filter container and flowing a fluid from the pre-filter container, through the pump and filter line, and into the post-filter container.

Filtration systems and methods generally described herein are particularly well-suited for use in connection with leukoreduction of blood or a blood component. However, filtration systems and methods described herein are not limited to use with specific fluids or filtration processes and may be applied to virtually any fluid treatment system involving filtration between two containers or groups of containers.

BRIEF DESCRIPTION OF THE DRAWINGS

FIG. 3 is a schematic view of an example filtration system and method similar to that shown in FIG. 1 but with a plurality of post-filter containers.

DESCRIPTION OF THE PREFERRED EMBODIMENTS

The embodiments disclosed herein are exemplary of the invention, which may be embodied in various forms, and specific details disclosed herein are not to be interpreted as limiting the invention.

Figure 1:
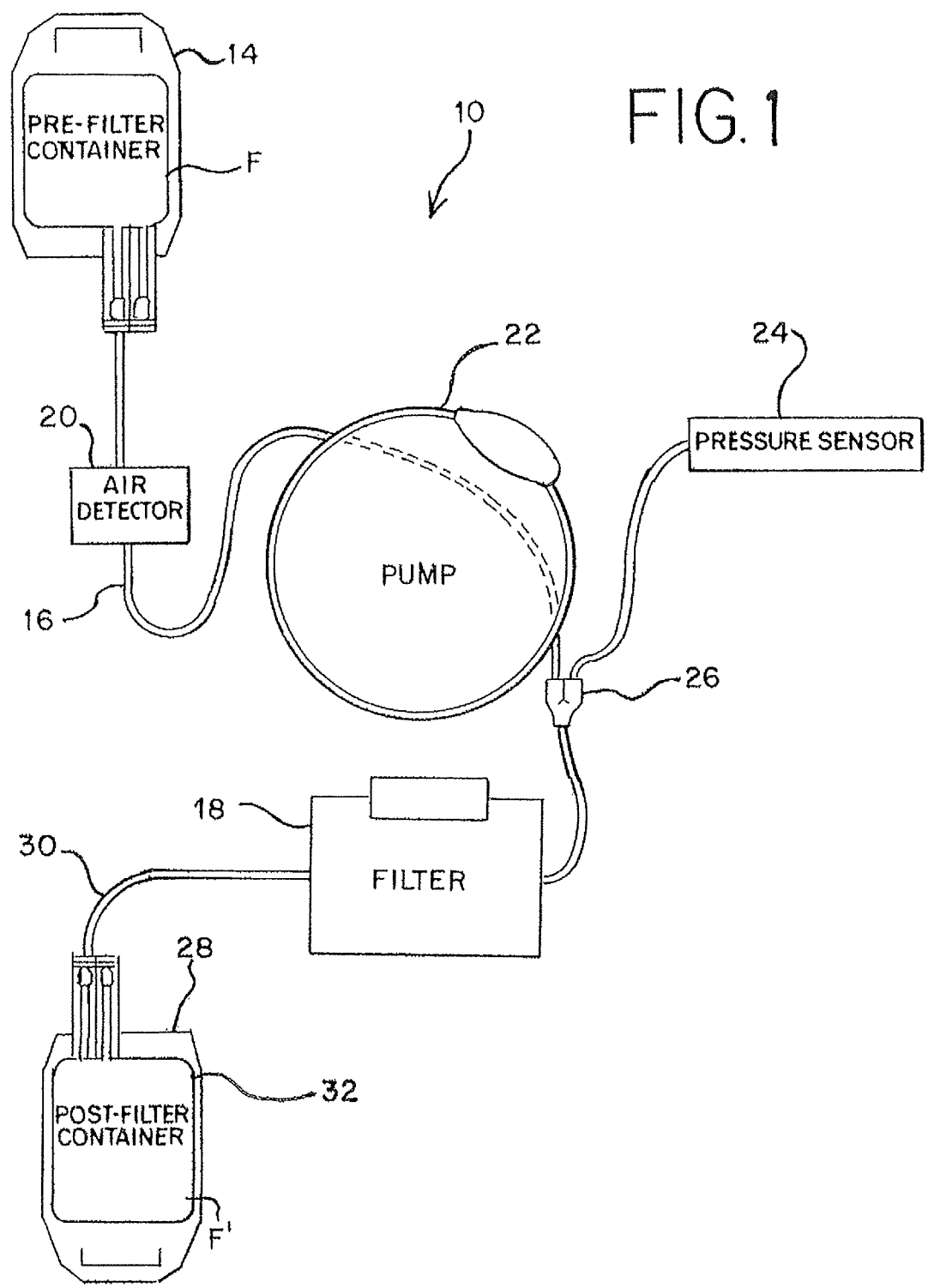
FIG. 1 is a schematic view of an example filtration system that provides automated pre-filtration air management and a method of using the same.
Figure 2:
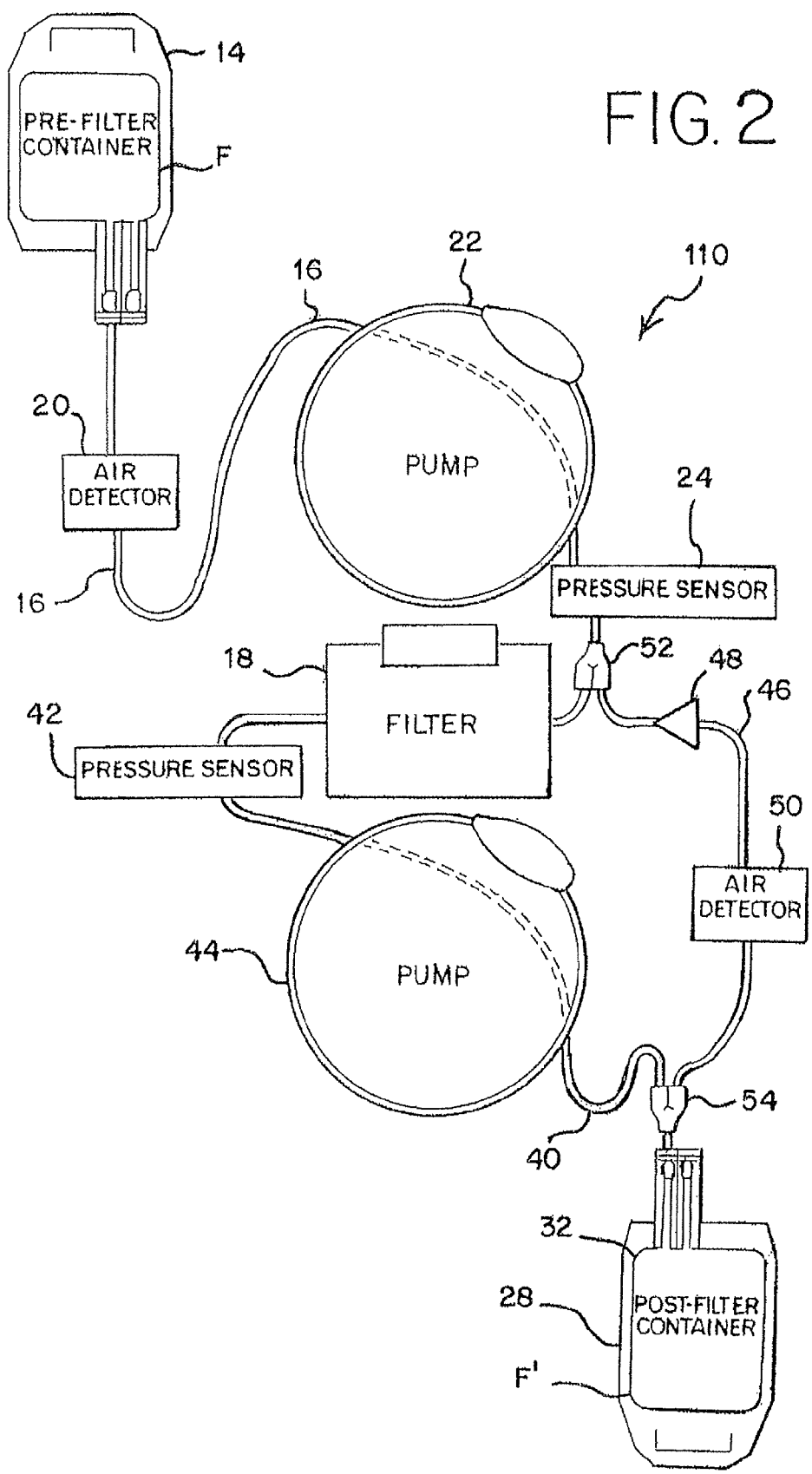
FIG. 2 is a schematic view of another example filtration system that provides automated pre-filtration air management and a method of using the same.

FIGS. 1-3 illustrate exemplary automated filtration systems that utilize pumps and pressure sensors to provide pre-filtration air management to reduce the amount of air in a post-filtration product. Thus, contrary to the typical efforts discussed above to remove air only after filtration, or by use of gravity or manual retro-priming, the example systems and methods of FIGS. 1-3 are adapted to evacuate the air by use of a pump prior to filtration. The examples described herein also include apparatus and methods for controlling the filtration rate to reduce the filtration time and to improve the predictability of the time required for filtration. The example systems 10 and 10' illustrated in FIGS. 1 and 3, respectively, use a single pump and pressure sensor, while the example system 110 illustrated in FIG. 2 uses two pumps and two pressure sensors to avoid exclusively pushing or pulling fluid through a filter. It will be appreciated from the following description that automated pre-filtration air management may be used with a wide range of filtration systems, including those systems comprising a component of a larger fluid processing set.

The filtration system 10 of FIG. 1 includes a pre-filter container 14 adapted to contain a fluid "F", for example, a biological fluid such as whole blood or a component of whole blood. The pre-filter container 14 may include a needle and associated tubing (not shown) for drawing an amount of fluid into the container 14, although any method of filling the pre-filter container 14 may be used without departing from the scope of the present invention. The pre-filter container 14 may be made of a flexible, transparent material, such as polyvinyl chloride (typically plasticized), other medical grade plastic, or alternative suitable materials. The pre-filter container 14 also may include other ports connectable to various peripheral devices, such as by tubing, including for example other fluid containers. The exact structure of the pre-filter container 14 is not intended to limit the scope of the present invention and may vary from the particular structures described and illustrated herein.

The pre-filter container 14 is connected to a first end of a length of tubing, referred to herein as a filter inlet flow path 16, which may include a frangible cannula (not shown) that can be broken to permit flow from the pre-filter container 14 through the filter inlet flow path 16, or flow in the opposite direction. The second end of the filter inlet flow path 16 is connected to a filter 18. A suitable filter media (not shown) is located within the filter 18 so that fluid passing from the filter inlet flow path 16 through the filter 18 is suitably filtered. The exact structure and function of the filter 18 is not intended to limit the scope of the present invention, but a leukoreduction filter is one example of a filter that would be suitable for use in combination with a biological fluid "F" comprising blood or a blood component. For example, the leukoreduction filters in the Sepacell® line from Asahi Kasei Medical Co., Ltd. of Tokyo, Japan are suitable for use with the example fluid filtration systems according to the present invention.

The filter inlet flow path 16 further includes an optical sensor or air detector 20 that can be of any suitable configuration to monitor the initiation and completion of the flow of fluid, through sensing of the presence of air or liquid through the filter inlet flow path 16 and to provide a signal to a microprocessor (not shown). Between the air detector 20 and the filter 18 is a pump 22, which may be a non-occlusive or occlusive pumping mechanism. In the illustrated embodiment, an occlusive pumping mechanism, a peristaltic pump, is shown and may accept a portion of the tubing of the filter inlet flow path 16. The signal from the air detector 20 is used by the microprocessor (not shown) in controlling the pump 22, as described below in further detail. The filter inlet flow path 16 also includes a pressure sensor 24, shown for example between the pump 22 and the filter 18. The pressure sensor 24 is shown as being connected to the filter inlet flow path 16 by a Y-junction 26, however, it will be appreciated by one of ordinary skill in the art that the pressure sensor may be of a configuration that is inline or is incorporated into a housing of the filter 18, or other suitable alternative configurations may be used. In any of these configurations of a pressure sensor 24, the pressure sensor will essentially measure the pressure in the filter inlet flow path 16.

The pressure sensor 24 also provides a signal that is communicated to the microprocessor (not shown) that is adapted, in turn, to control the speed of the pump 22. Control of the speed of the pump 22 determines the flow rate through the pump 22. The pressure sensor 24 and pump 22 can thereby be used to optimize the filtration procedure to produce rapid and efficient filtration, without damaging the fluid or filter 18. Filtration time can be reduced dramatically, such as to several minutes, while simultaneously increasing the predictability of the processing time. The flow rate control also avoids potential damage to the filter 18, as well as to the filtered fluid product, such as by the hemolysis that can take place with respect to red blood cells in a blood product.

The filter 18 further is connected to a post-filter container 28 by a length of tubing, referred to herein as a filter outlet flow path 30. The post-filter container 28 is adapted to receive and contain a filtered fluid "F'" and is made of a flexible, preferably transparent material, such as the suitable materials described above in reference to the pre-filter container 14. The post-filter container 28 defines an interior volume or portion 32 that may be expandable because of, for example, stretching of the plastic from a minimum volume to a maximum volume by receipt of filtered fluid "F'". During storage, transport, and before filtration has commenced, the post-filter container 28 is substantially flat and at or near a minimum volume. As the post-filter container 28 is filled with an increasing amount of fluid "F'", it will continually expand and increase in volume, up to a maximum volume in which the post-filter container 28 generally resembles a pillow or teardrop. Also, the tubing set for use in the system 10 preferably is sterilized prior to use in a filtration procedure, most preferably during the manufacturing process prior to packaging and transport.

The post-filter container 28 may include a plurality of ports (not shown) that are connectable, such as by tubing, to various peripheral devices, including other fluid containers. As illustrated with the system 10' shown in FIG. 3, a plurality of post-filter containers, for instance containers 28, 28' and 28", may be coupled together in a multi-sectional filter outlet flow path 30' to split a large pre-filtration quantity into two or more filtered products. For example, a single 600 ml jumbo pre-filtration quantity could be filtered and split into three 200 ml post-filtration products. In such instances, the post-filtration containers may be coupled together and hung at the same height to permit self-leveling among the containers. Thus, such multiple container sets may be used in procedures such as random donor platelet collections that include combining of fluids from multiple pre-filter containers, or post-filtration further fluid separation into satellite containers via centrifugation or other processing.

The system 10 also may include further components as desired, such as tubing segments (not shown) in the filter outlet flow path 30. The tubing segments may be provided to obtain samples of the post-filtered fluid "F'", such as may be desirable when the system 10 is used to process blood or a blood component. The segments may store a quantity of filtered fluid apart from the fluid in the post-filter container 28. The stored fluid in the segments generally would be used for testing prior to use of the fluid in the post-filter container 28. As will be appreciated by one of ordinary skill in the art, the structure of the segments may vary and may comprise short tubing portions (such as, for example, two- or three-inches long) that may be uniquely labeled for each filtration system 10, to ensure traceability. Each segment may be sealable and severable from the remainder of the tubing to allow for testing of the fluid "F'" contained therein prior to transfusion or other use of the filtered fluid "F'" in the post-filter container 28. An example of such tubing segments for obtaining samples is shown and described in U.S. patent application Ser. No. 11/618,286, which is hereby incorporated herein by reference.

A method of using the example filtration system 10 illustrated in FIG. 1 will now be described. In accordance with a method of using the above described system 10, the pre-filter container 14 contains a fluid "F" and is suspended or held in an upright or at least an inclined position so as to allow air within the pre-filter container 14 to naturally rise above the higher density fluid "F" in the pre-filter container 14, while also allowing the fluid "F" to exit the container and move into the filter inlet flow path 16 that is connected at a lower position on the pre-filter container 14. Note, however, that if an occlusive pumping mechanism is used for the pump 22 for the pre-filtration evacuation of air and for the filtration process, this permits the other components within the system 10 to be located essentially at any relative height and in any orientation relative to the pre-filter container 14, as opposed to the need with prior art systems to hang components at specific elevations relative to one another and so as to have the air rise within the components. This is due to the fact that if an occlusive pumping mechanism is used, the tubing will be occluded and thus fluid movement will only occur when pump movement occurs. This permits an advantage of being able to design and package a more compact system, with the components requiring substantially less vertical space.

When first installed, air is present in the filter 18, post-filter container 28, and filter outlet flow path 30. Before filtration begins, this air is evacuated into the pre-filter container 14 via operation of the pump 22 in a first flow direction. If the fluid inlet flow path 16 includes a cannula it is broken to allow passage through the inlet flow path 16 prior to operating the pump 22. When the air reaches the pre-filter container 14, it will flow through and rise to a level above the fluid "F" in the pre-filter container 14. The pressure sensor 24 may be used to control the pump 22 to evacuate the air by operating the pump 22 until a particular negative pressure has been achieved. If necessary to achieve sufficient air removal, evacuation may continue to a point where the post-filter fluid path 30 reversibly collapses, depending on the physical and structural properties of the fluid path material selected.

The specific negative pressure required for adequate evacuation will be based on the relative quantity of air considered acceptable to be present in the post-filter container 28 for subsequent storage of the fluid "F'". The correspondence between specific negative pressures and the quantities of air that remain in a post-filter container will be dependent on the particular construction and configuration of the system 10. Alternatively, the pump 22 may be operated for a set period of time to achieve the desired evacuation of air, after a determination of the time required to achieve a desired level of evacuation for a particular construction and configuration of a system 10.

After evacuation of the air, the pump 22 reverses direction so as to transfer the fluid "F" from the pre-filter container 14, through the filter 18, and to then be delivered as filtered fluid "F'" into the post-filter container 28. The flow of the fluid "F" is dependent on the rate of pumping, which is based on the speed of the pump 22. The speed of the pump 22 is, in turn, dependent on the signal from the pressure sensor 24 which monitors the pressure build up in the filter 18 that is communicated into the filter inlet flow path 16. During filtration, the pressure sensor 24 checks the pressure generated by the resistance of the filter 18. Pressure is expected to proportionally increase with increased flow rate dependent on the inherent resistance of the filter material utilized. In some instances, high pressures in the filter 18 may cause harm to the fluid being filtered, such as the hemolysis of red blood cells. If the pressure sensor 24 indicates that the flow is generating a potentially damaging pressure level, then the pump speed will be reduced so as to reduce the flow. This will cause the pressure in the filter 18 to be reduced. The pressure sensor 24 will enable the pump 22 to filter the fluid as fast as possible while ensuring that the product remains safe and is effectively filtered. Thus, the pressure monitoring and corresponding control of the pump 22 helps to ensure that a quality filtered product is produced as transmembrane filter pressure may compromise the safety of the product and the reliability of the filtration.

The air detector 20 may be adapted to provide a signal once it determines that the pre-filter container 14 is empty or as air enters the filter inlet flow path 16. However, before filtration is completed, the pump 22 may be permitted to continue to operate for a short period of time to use the air which was transferred into the pre-filter container 14 before the start of filtration to clear the inlet of the filter 18, thus maximizing the recovery of the fluid "F" that is collected as filtered fluid "F'" in the post-filter container 28. The pump 22 may be stopped based on an alternative signal, such as a signal from the pressure sensor 24 that may indicate when there has been a significant reduction in the pressure in the filter 18, as will occur once the fluid has been recovered from the filter 18. Due to the pre-filtration evacuation of air, there generally is no post-filtration need to "burp" or otherwise purge air from the post-filter container 28.

Once the pump 22 has stopped, the post-filter container 28 may be sealed and severed from the filter outlet flow path 30. The operator also may take other actions as desired, such as to seal and/or sever the segments, if utilized, so as to provide discrete fluid test samples associated with the post-filter container 28. The sealing and severing process may be automated as desired. The filtered fluid "F'" in the post-filter container 28 may be stored, delivered to a recipient, or otherwise processed. For example, if the fluid "F" is whole blood and the filter 18 is a leukoreduction filter, one common post-filtration process is centrifugation of the post-filter container 28.

It will be appreciated that use of the pump 22 and pressure sensor 24 may result in numerous advantages, such as more rapid and predictable filtration, without risk of damage to the filter or fluid due to potentially excessive pressures. There are very few steps needed to perform and complete a filtration. Operator intervention and manipulation may not be needed during the pre-filtration removal of air or thereafter during filtration. No effort is needed subsequent to the filtration to purge air from the post-filter container 28. No further manipulations, such as bending down, squeezing a container, etc. are necessary to carryout the procedures. Thus, there is required minimal physical effort and cognitive load (ergonomic, ease of use, and minimal opportunities for misuse). Also, the filling of the optional line segments, if present, is automatic, and does not require pre- or retro-priming. Moreover, as mentioned above, the components may be arranged essentially at a common height, with the only limitation being that the pre-filter container 14 should be in an inclined or upright position to keep any air above any fluid in the container. This flexibility in configuring the system 10 may permit an operator to load, operate and unload the system from a comfortable, ergonomic position.

In a further alternative, the system 10 may be used for pre-filtration evacuation of air followed by pre-filtration pump-assisted retro-priming. Thus, by starting with a fluid "A" in the post-filter container 28, such as Ad-Sol or another suitable solution, the pre-filtration evacuation of air via the pump 22 from the post-filter container 28, filter outlet flow path 28 and filter 18 can be immediately followed by the pump 22 continuing to draw a vacuum until some of the fluid "A" is moved through the filter outlet flow path 30, filter 18 and at least a portion of the filter inlet flow path 16, thereby assuring the removal of air from these portions of the system 10 as the liquid "A" displaces the air into the pre-filter container 14. The retro-priming may be automated and continue until the air detector 20 senses the presence of the fluid "A", at which time a signal is sent to the microprocessor (not shown), which would control the pump 22 to stop and reverse the pump 22. Upon reversal, the pump 22 would begin the flow of the additional fluid "F" from the pre-filter container 14 for filtration. Depending on the relative volumes of the components of the system 10, such pump-assisted retro-priming may continue until some of the fluid "A" enters the pre-filter container 14. With this alternative, the post-filter container 28 must be in an upright orientation (air on top and liquid on bottom) for the method to work.

The example system 10 also may provide advantages associated with the components required. For instance, few components are needed and additional components, such as a bypass line having a corresponding one-way valve and clamps or other closure devices associated therewith are not needed because the transfer of air occurs through the filter 18 itself before it ever comes into contact with any liquid. The post-filter container 28 also need not be constrained or otherwise have its capacity limited. Indeed, the post-filtration container 28 may vary in size based on user comfort and design performance. This system 10 and method of filtration and air management also is not limited in what can be filtered. Thus, it is capable of utilizing both soft housing filters and hard or rigid housing filters. This can be significant in that some procedures, such as leukoreducing red blood cells require use of a soft housing filter, while filtering whole blood typically requires use of a hard housing filter. The pump 22 also may be of the peristaltic type, which permits fine control and low pulsations to keep the filtered fluid safe, or of another suitable type.

It should be noted that the system 10 alternatively may operate without the use of the air detector 20. In this alternative, the pressure sensor 24 signals the end of filtration because as the pre-filter container 14 empties, the pressure in the filter 18 drops significantly. Thus, a signal from the pressure sensor 24 may be used to assist in achieving sufficient recovery of fluid from the filter 18.

A further example of a filtration system is illustrated in the system 110 shown in FIG. 2. The example filtration system 110 illustrated in FIG. 2 includes a pre-filter container 14 adapted to contain a fluid "F", a filter inlet flow path 16, filter 18, air detector 20, pump 22, pressure sensor 24 and post-filter container 28 having an interior portion 32 adapted to receive filtered fluid "F'". The system 110 also may include a frangible cannula (not shown) in the filter inlet flow path 16. These components of the system 110 may be similar to those shown in the system 10 of FIG. 1. However, the system 110 in FIG. 2 further includes a filter outlet flow path 40 that includes a second pressure sensor 42 and a second pump 44. The pressure sensors 24 and 42 are shown as being inline sensors, although it will be appreciated that the sensors could be configured to be connected to the system 110 via additional connectors, such as the Y-junction 26 that is illustrated in the system 10 of FIG. 1.

The system 110 is shown with an optional bypass flow path 46 having a one-way valve 48 and a second air detector 50. The optional bypass flow path 46 is connected at a first end to the filter inlet flow path 16 via a first Y-junction 52 and is connected at a second end to the filter outlet flow path 40 via a second Y-junction 54. The bypass flow path 46 is not needed if the air is adequately evacuated to the pre-filter container 14 by use of the pump 22 prior to filtration, as described above with respect to the system 10 shown in FIG. 1. However, the bypass flow path 46 shown in the system 110 of FIG. 2 may otherwise be used to ensure complete removal of air from the post-filter container 28 by permitting excess air in the post-filter container 28 to travel through the bypass flow path 46 to the filter inlet flow path 16 where it may assist in obtaining recovery of fluid through the filter 18. The one-way valve 48 ensures that unfiltered fluid "F" is not permitted to contaminate the filtered fluid "F'" that is collected in the post-filer container 28.

A clamp or other closure device (not shown) may be used in the bypass flow path 46 to control the opening and closing of the bypass flow path 46 to prevent the premature flow of filtered fluid "F'" from entering the bypass flow path 46. If a bypass flow path 46 is used, the completion of the post-filtration evacuation of any air from the post-filter container 28 will be communicated to the microprocessor (not shown) by a signal from the air detector 50 when it detects the presence of fluid entering the bypass flow path 46. The clamp or other closure device (not shown) in the bypass flow path 46 may be opened to allow the excess air in the post-filter container 28 to be purged by flowing upward through the bypass flow path 46 and into the filter inlet flow path 16. This movement of air into the filter inlet flow path 16 assists in the further recovery of fluid through the filter 18, without the difficulties associated with manual squeezing of the post-filter container 28 to "burp" the container. Indeed, the closure device (not shown) optionally may be adapted to be in operative communication with the microprocessor (not shown) to automate the air removal process. The air that is directed into the bypass flow path 46 is effectively "reused" to recover further fluid from the filter 18. Thus, after the flow from the pre-filter container 14 ceases, the closure device (not shown) in the bypass flow path 46 is opened. By simply opening the closure device, the system 110 automatically relieves pressure in the post-filter container 28 and recycles the post-filter air to the inlet flow path 16 to recover further fluid from the filter 18.

During operation of the system 110, the signals from the first pressure sensor 24 and second pressure sensor 42 are communicated to a microprocessor (not shown) to control the speeds of the respective first pump 22 and second pump 44. While the first pump 22 attempts to push the fluid "F" through the filter 18, the second pump 44 attempts to pull the filtered fluid "F'" through the filter 18. This dual pump configuration provides improved control of trans-membrane pressure over the use of a single pump to move fluid through the filter 18. The second pressure sensor 42 downstream of the filter 18 regulates the speed of the second pump 44 to avoid generating a vacuum through the filter 18. The dual pump configuration not only provides the advantages discussed above in relation to the system 10 of FIG. 1, but also should yield faster filtration, due to the smaller pressure differential in the filter, while also providing a greater recovery of fluid because the second pump 44 can be utilized to further clear the outlet face of the filter 18. The first pump 22 and second pump 44 may alternatively be driven by a common drive unit (not shown), but configured to have different flow rates as desired to achieve appropriate relative pressures into and out of the filter 18.

When the filtration and recovery are complete, the pumps 22 and 44 are stopped. As discussed above with respect to the system 10 of FIG. 1, the system 110 of FIG. 2 then may be sealed and severed from the filter outlet flow path 40. The operator also may take other actions as desired, such as manual pump activation for additional removal of residual air, and/or such as to seal and/or sever any optional segments, so as to provide discrete fluid test samples associated with the post-filter container 28. The filtered fluid "F'" in the post-filter container 28 may be stored, delivered to a recipient, or otherwise processed. For example, if the fluid "F'" is whole blood and the filter 18 is a leukoreduction filter, one common post-filtration process is centrifugation of the post-filter container 28. It will be appreciated that, as discussed above with respect to the single pump system 10 of FIG. 1, the dual pump system 110 of FIG. 2 also may utilize pump-assisted retro-priming. In such an alternative, either pump 24 or pump 44, or both may be operated during the retro-priming procedure to assist in evacuating the air from the system and moving a solution from the post-filter container 28 to the filter inlet flow path 16 and/or to the pre-filter container 14, prior to starting the filtration of the fluid "F."

Fluid filtration using a post-filter container 28 according to the disclosure set forth herein may be accomplished using any of the systems generally illustrated by the examples in FIGS. 1-3, alternatives described herein, or by any other filtration system involving the transfer of fluid from a source (typically a pre-filter container), through a fluid conduit having a filter or fluid treatment device, to a post-filter container. It is preferable to provide a pump and pressure sensor to reduce the time required for filtration and to improve the predictability of the time required to complete the process. Air removal also may be achieved via pre-filtration evacuation of air, and/or fluid via use of a pump. Note that, as is common in blood center back lab settings, the system may be "ganged" in a sequence of multiple units with individual or common microprocessor control. For example, as is also common in blood center back lab settings, a six-position centrifuge could be utilized adjacent to a six station processing station for optimal efficiency in product manipulation. A multiple unit system such as this would provide efficiencies of space, labor and regulatory compliance.

A wide variety of fluid filtration methods using a pre-filter container, a filter or fluid treatment device, and a post-filter container are well-known to those of ordinary skill in the art and may be practiced with a post-filter container according to the above disclosure.

It will be understood that the embodiments described above are illustrative of some of the applications of the principles of the present invention. Numerous modifications may be made by those skilled in the art without departing from the spirit and scope of the invention, including those combinations of features that are individually disclosed or claimed herein. For these reasons, the scope of the invention is not limited to the above description.

The invention claimed is:

1. A method for (a) preparing a filtration system and (b) filtering a fluid through said system, said system including a filter, a pre-filter container containing fluid to be filtered, a post-filter container, a first pump between said filter and said pre-filter container, an air detector, a first pressure sensor, a second pump and second pressure sensor in communication with the filter and the post-filter container and a flow path between said pre-filter container and said post filter container, said method comprising:
    evacuating air from at least a portion of the filter, the post-filter container and said flow path into the pre-filter container by action of said pumps;
    operating said pumps in selected flow directions until a desired evacuation of air from said flow path or said post-filter container has been achieved; and
    flowing a fluid from said pre-filter container to said post-filter container by coordinated operation of said first and second pumps.

2. The method of claim 1, wherein the system further comprises a filter inlet flow path and a filter outlet flow path, said method further comprising permitting air to move from said filter outlet flow path into the filter inlet flow path.

3. The method of claim 1 comprising automatically commencing said flow of the fluid from the pre-filter container and into the post-filter container after the step of flowing air from the filter into the pre-filter container.

4. The method of claim 3, comprising reversing said first pump to automatically flow the fluid from the pre-filter container, through the first pump and flow path, and into the post-filter container after said flowing air from the filter into the pre-filter container.

5. The method of claim 1, further comprising monitoring the presence of fluid flowing from the pre-filter container; detecting a signal from the air detector; and stopping the pump that is in communication with the pre-filter container and the filter in response to said signal.

6. The method of claim 1 comprising detecting the pressure at said filter and adjusting the speed of one or both of said pumps in response to said detected pressure.

7. The method of claim 2 further comprising detecting the presence of air entering said filter inlet flow path.

8. The method of claim 7 comprising continuing to operate at least one of said pumps after air has been evacuated from said pre-filter container.

9. The method of claim 1 comprising detecting a reduction in the pressure at said filter and adjusting the speed of at least one of said pumps in response to said detection.

10. The method of claim 2 further comprising priming said system after said evacuating.

11. The method of claim 10 wherein said post-filter container contains a solution, said method further comprising priming said system with a solution from said post-filter container.

12. The method of claim 11 comprising detecting the presence of said solution in said flow path.

13. The method of claim 12 further comprising priming said system until the solution is detected in said air detector of said filter inlet flow path.

14. The method of claim 1 comprising detecting pressure at said first and second pressure sensors and adjusting pump speeds of said first and second pumps.

15. A method for (a) preparing a filtration system and (b) filtering a fluid through said system, said system including a filter, a pre-filter container containing fluid to be filtered, a post-filter container, a filter inlet flow path and a filter outlet flow path, a first pump between said pre-filter container and said filter and a second pump between said filter and said post-filter container, and a first pressure sensor on said filter inlet flow path and a second pressure sensor on said filter outlet flow path, and a by-pass line between said post-filter container and said filter inlet flow path, said method comprising:
  evacuating air from said post-filter container through said by-pass line;
  flowing fluid from said pre-filter container through the flow path by action of said pump;
  flowing said evacuated air from said by-pass line into said filter inlet flow path
  detecting signals from said first and second pressure sensors; and adjusting said first and second pumps in response to said signals.

16. The method of claim 1 further comprising sending a signal to a microprocessor when air evacuation is completed.

17. The method of claim 15 wherein said by-pass line includes a one way valve.

* * * * *